United States Patent [19]

Bjorkquist

[11] Patent Number: 4,981,557

[45] Date of Patent: Jan. 1, 1991

[54] TEMPORARY WET STRENGTH RESINS WITH NITROGEN HETEROCYCLIC NONNUCLEOPHILIC FUNCTIONALITIES AND PAPER PRODUCTS CONTAINING SAME

[75] Inventor: David W. Bjorkquist, Wyoming, Ohio

[73] Assignee: The Procter & Gamble Company, Cincinnati, Ohio

[21] Appl. No.: 343,777

[22] Filed: Apr. 26, 1989

Related U.S. Application Data

[63] Continuation-in-part of Ser. No. 215,087, Jul. 5, 1988, abandoned.

[51] Int. Cl.$^5$ .............................................. D21H 17/45
[52] U.S. Cl. ................... 162/168.2; 162/111; 162/112; 162/168.5
[58] Field of Search ............... 162/164.6, 168.2, 168.3, 162/168.4, 168.5, 112, 111

[56] References Cited

U.S. PATENT DOCUMENTS

| | | | |
|---|---|---|---|
| 3,079,296 | 2/1963 | Houff et al. | 162/168 |
| 3,093,506 | 6/1963 | Tsatsos | 117/155 |
| 3,096,228 | 7/1963 | Day et al. | 162/112 |
| 3,317,370 | 5/1967 | Kekish | 162/168 |
| 3,410,828 | 11/1968 | Kekish | 260/67.5 |
| 3,556,932 | 1/1971 | Coscia et al. | 162/166 |
| 3,740,391 | 6/1973 | Williams et al. | 260/233.3 |
| 3,772,407 | 11/1973 | Williams et al. | 260/375 |
| 3,819,555 | 6/1974 | Kaufman | 260/29.4 |
| 4,233,411 | 11/1980 | Ballweber et al. | 525/155 |
| 4,603,176 | 7/1986 | Bjorkquist et al. | 525/329.4 |
| 4,605,702 | 8/1986 | Guerro et al. | 525/154 |
| 4,675,394 | 6/1987 | Solarck et al. | 536/43 |

FOREIGN PATENT DOCUMENTS 0133699 6/1985 European Pat. Off. .

OTHER PUBLICATIONS

*Surfaces Coatings Related Paper Wood*, Symp. "Mechanisms of Wet-Strength Development in Paper", Syracuse, N.Y., 1967, 269–299 (Eng.).

*Cellulose Chemistry and Technology*, I. A Survey of "Mechanisms of Wet-Strength Development", Lars Westfelt, 13, 813–825 (1979).

*Primary Examiner*—Peter Chin
*Attorney, Agent, or Firm*—Leonard W. Lewis; Jerry J. Yetter

[57] ABSTRACT

Temporary wet strength resins, and paper products containing same, having a molecular weight of from about 20,000 to about 200,000, most preferably from about 30,000 to aboug 95,000 having the fomula:

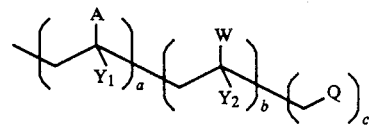

wherein: A is 0 or

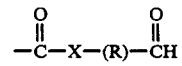

and X is —O—, —NH—, or —NCH$_3$—, and R is a substituted or unsubstituted aliphatic group; Y$_1$ and Y$_2$ are independently —H, —CH$_3$, or a halogen; W is a nonnucleophilic, water-soluble nitrogen heterocyclic moiety; and Q is a cationic monomeric unit. The mole percent of "a" ranges from about 30% to about 70%, preferably from about 45% to about 55%; the mole percent of "b" ranges from about 30% to about 70%, preferably from about 45% to about 55%; and the mole percent of "c" ranges from about 1% to about 40%, most preferably from about 2% to about 5%.

10 Claims, No Drawings

TEMPORARY WET STRENGTH RESINS WITH NITROGEN HETEROCYCLIC NONNUCLEOPHILIC FUNCTIONALITIES AND PAPER PRODUCTS CONTAINING SAME

This application is a continuation-in-part of application Ser. No. 215,087 filed July 5, 1988 now abandoned.

TECHNICAL FIELD

This invention relates to wet strength resins which can impart temporary wet strength to paper products, and to paper products having temporary wet strength.

BACKGROUND OF THE INVENTION

Wet strength is a desirable attribute of many disposable paper products, such as napkins, paper towels, household tissues, disposable hospital wear, etc. which come into contact with water in use. However, an untreated cellulose fiber assemblage will typically lose 95% to 97% of its strength when saturated with water. To improve the wet strength paper manufacturers in the past have added wet strength resins during the paper making process.

These wet strength additives have typically resulted in paper products with permanent wet strength, i.e., paper which when placed in an aqueous medium retains a substantial portion of its initial wet strength over time. Permanent wet strength in paper products is often an unnecessary and undesirable property. Paper products such as toilet tissues, etc., are generally disposed of after brief periods of use into septic systems and the like. Clogging of these systems can result if the paper product permanently retains its hydrolysis-resistant strength properties.

More recently, manufacturers have added temporary wet strength additives to paper products for which wet strength is sufficient for the intended use, but which then decays upon soaking in water. Decay of the wet strength facilitates flow of the paper product through septic systems.

As recognized in the pertinent literature relating to wet strength of paper products, such as Stannet, "Mechanisms of Wet Strength Development in Paper," Surface Coatings Related Paper Wood symposium, pp. 289–299 (1967) and Westfelt, "Chemistry of Paper Wet Strength. I. A survey of "Mechanisms of Wet Strength Development," Cellulose and Chemistry and Technology, Vol. 13, pp. 813–825 (1979), paper products develop dry strength in part due to interfiber hydrogen bonding. When the paper product is wetted, water disrupts the hydrogen bonds and, as a consequence, lowers the strength of the paper product. Historically, wet strength of paper products has been increased primarily by two approaches. One approach is to prevent water from reaching and disrupting the hydrogen bonds, for example, by coating the paper product. Another approach is to incorporate additives in the paper product which contribute toward the formation of interfiber bonds which are not broken or, for temporary wet strength, which resist being broken, by water. The second approach is the technique of choice, especially for tissue products. In this latter approach, a water soluble wet strength resin is added to the pulp, generally, before the paper product is formed (wet-end addition). The resin generally contains cationic functionalities, so that it can be easily retained by the cellulose fibers, which are naturally anionic.

A number of resins have been used or disclosed as being particularly useful for providing wet strength to paper products. These include urea-formaldehyde and melamine-formaldehyde resins. Such resins have limited wet strength decay. Polyamide-epichlorohydrin resins have also been used in paper products. However, they also provide little wet strength decay.

Numerous approaches for providing paper products claimed as having good initial wet strength which decays significantly over time have been reported.

Resins formed by reacting glyoxal (CHOCHO) with water-soluble vinylamide polymers are suggested as possessing temporary wet strength in U.S. Pat. No. 3,556,932, Coscia et al., issued Jan. 19, 1971. However, wet strength decay is reported only at alkaline pH levels—conditions not necessarily present in septic systems. Also, papers incorporating such resins lose only about half their wet strength upon exposure to water. Greater degrees of wet strength decay are desirable.

U.S. Pat. No. 3,740,391, Williams et al., issued June 19, 1973, describes a water-soluble thermosetting wet strength agent for paper which is prepared by reacting an amidated ionic glucopyranosyl compound with glyoxal. Paper products containing this wet strength agent lose about one half their original wet strength after soaking in water for 24 hours. Such wet strength decay is not sufficiently rapid since the paper products in which the resin is used, such as toilet paper, are generally disposed of within a few minutes use.

U.S. Pat. No. 4,605,702, Guerro et al., issued Aug. 12, 1986, discloses temporary wet strength resin made by reacting a vinylamide polymer with glyoxal, and then subjecting the polymer to an aqueous base treatment. The product is said to provide tissue paper which loses a part of its wet strength when soaked in water at neutral pH.

U.S. Pat. No. 4,603,176, Bjorkquist and Schmidt, issued July 29, 1986, discloses temporary wet strength resins made by reacting glyoxal with a cationic vinylamide copolymer. The cationic vinylamide copolymer is prepared from a nonnucleophilic, water-soluble monomer, such as dimethylacrylamide, an acrylamide nucleophilic monomer, and monomer containing a quaternary nitrogen. Subsequent to the reaction of glyoxal with the nucleophilic amide, the final product has from about 3% to about 65%, mole percent basis, of monomeric units with nucleophilic amide functionalities and about 1% to about 20%, mole percent basis, of monomeric units with glyoxal-substituted amide functionalities.

Modified starch temporary wet strength agents are marketed by the National Starch and Chemical Corporation (New York, New York). This type of wet strength agent can be made by reacting dimethoxyethyl-N-methyl-α-chloroacetamide with cationic starch polymers. Modified starch wet strength agents are also described in U.S. Pat. No. 4,675,394, Solarek, et al., issued June 23, 1987. Unfortunately, such wet strength agents typically deliver relatively high dry strength in conjunction with the level of wet strength provided. This is undesirable for products, such as tissue paper, for which softness is important, since increased dry strength generally is accomplished by decreased softness.

U.S. Pat. No. 3,410,828, Kekish, issued Nov. 12, 1968 and its parent, U.S. Pat. No. 3,317,370, Kekish, issued May 2, 1967, disclose wet strength resins which comprise water soluble copolymers of an aldehyde monomer, such as acrolein, and a nitrogen heterocyclic monomer containing an ethylenically unsaturated group capable of polymerization with aldehydes. The advantages of these copolymers, as set forth in their respective patent disclosures, is that retention aids (such as aluminum salts), are not needed because the copolymers have no anionic character. Optionally, the copolymers can be made cationic by reacting a water soluble amine or quaternary amine with the copolymers. The disclosures of these patents generally link increased molecular weight with increased effectiveness without consideration of the particular properties and characteristics desirable for temporary, as opposed to permanent, wet strength.

In spite of the technology described above, there exists a continuing need to provide temporary wet strength resins having increased wet strength decay rates.

U.S. Pat. No. 3,096,228, Day et al., issued July 2, 1983, describes paper products wherein a solution of glyoxal is applied to a paper web. Upon exposure to water, this paper described as being is able to resist a rupture for only about a minute and as disintegrating within about 3 minutes. While this approach using glyoxal monomers provides rapid wet strength decay, it does not provide paper products with sufficient initial wet strength or sufficient retention of wet strength over the period of intended use.

It is an object of this invention to provide improved temporary wet strength resins that can provide paper products with high levels of initial wet strength and which retain sufficient strength during the period of intended use, but which also facilitate wet strength decay such that very low strength levels are attained subsequent to the period of intended use.

It is a further object of this invention to provide such wet strength characteristics as described above, without incurring larger increases in dry strength that typically incurred for known non-starch based temporary wet strength resins.

SUMMARY OF THE INVENTION

The temporary wet strength resins of the present invention comprise water-soluble, cationic polymers which have average molecular weights of from about 20,000 to about 200,000, preferably from about 30,000 to about 115,000, more preferably from about 30,000 to about 95,000, and are of the formula:

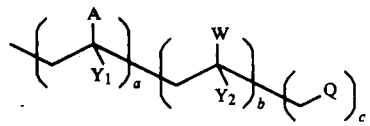

wherein: A is

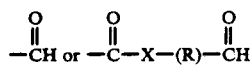

and X is —O—, —NH—, or —NCH$_3$—, and R is a substituted or unsubstituted aliphatic group; Y$_1$ and Y$_2$ are independently —H, —CH$_3$, or a halogen; W is a nonnucleophilic, water-soluble nitrogen heterocyclic moiety; and Q is a cationic monomeric unit. The mole percent of "a" ranges from about 30% to about 70%, preferably from about 45% to about 55%; the mole percent of "b" ranges from about 30% to about 70%, preferably from about 45% to about 55%; and the mole percent of "c" ranges from about 1% to about 40%, preferably from about 2% to about 20%, more preferably from about 2% to about 8%. The invention also encompasses paper products containing these resins.

DETAILED DESCRIPTION OF THE INVENTION

The temporary wet strength resins of the present invention comprise water-soluble, cationic polymers which have molecular weights of from about 20,000 to about 200,000, preferably from about 30,000 to about 115,000, more preferably from about 30,000 to about 95,000, and are of the formula:

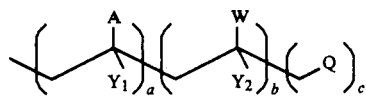

wherein: A is

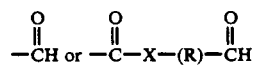

and X is —O—, —NH—, or —NCH$_3$—, and R is a substituted or unsubstituted aliphatic group; Y$_1$ and Y$_2$ are independently —H, —CH$_3$, or a halogen, such as Cl or F; W is a nonnucleophilic, water-soluble nitrogen heterocyclic moiety; and Q is a cationic monomeric unit. The mole percent of "a" ranges from about 30% to about 70%, preferably from about 45% to about 55%, the mole percent of "b" ranges from about 30% to about 70%, preferably from about 45% to about 55%; and the mole percent of "c" ranges from about 1% to about 40%, preferably from about 2% to about 20%, more preferably from about 2% to about 8%.

The resins of the present invention are further characterized by the substantially complete absence of nucleophilic functionalities attached to the polymer backbone that can react to form crosslink bonds with aldehydes.

As used herein, the term "substantially complete absence" shall mean that the polymer contains less than 3 mole percent of monomer units having nucleophilic functionalities attached thereto. Preferably, the polymer contains less than about 1 mole percent of such monomer units; and more preferably, zero mole percent of such monomer units.

Unless otherwise specified, all molecular weight values herein refer to the average weight molecular weight. Unless otherwise expressly specified, values for a, b, and c shall be mole percentage values based upon the average number of monomer units in the polymer chain.

As defined herein, the term "nonnucleophilic functionality" shall mean functional groups which do not form stable, covalent bonds with electrophilic functionalities (e.g., aldehydes) under chemical and physical conditions conventionally experienced during papermaking or during storage or use of paper products containing the resins of the present invention.

The monomeric units containing A and W and the monomeric unit, Q, are randomly distributed throughout the polymer in ratios corresponding to the mole percentage ranges described herein.

The cationic monomer unit Q can be derived from any polymerizable monomer which imparts a positive charge to the resin subsequent to polymerization. Cationic monomers suitable for use for the present invention are those which carry a positive electrostatic charge when dissolved in water. The counterion can be chloride, fluoride, bromide, iodide, sulphate, methylsulfate, phosphate and the like. Preferably, Q is hydrophilic and is an amine. Preferred cationic monomers include (p-vinylphenyl)trimethyl ammonium chloride, 2-(dimethylamino)ethyl acrylate, trimethyl(p-vinylbenzyl)ammonium chloride, p-dimethylaminoethylstyrene, dimethylaminopropyl acrylamide, 2-methylacryloxyethyltrimethylammonium methylsulfate, and 3-(methacryloylamino)propyl trimethyl ammonium chloride. There is preferably between about 1 mole % and about 40 mole % of the cationic monomer unit present in the resin backbone. More preferably, there is between about 2 mole % and about 20 mole % of the cationic monomer unit present, most preferably between about 2 mole % and about 8 mole %.

The non-nucleophilic functionality W can be incorporated into the polymer by polymerization with any monomer of the formula

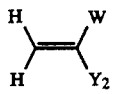

wherein W and $Y_2$ are as defined above, with $Y_2$ preferably being —H. Preferably, W is hydrophilic, or at least does not make the polymer hydrophobic.

Suitable monomers having nitrogen heterocyclic groups attached thereto for use in the present invention include vinyl oxazolidones, vinyl imidazoles, vinyl imidazolines, vinyl pyridines, and vinyl pyrrolidones, such as N-vinyl pyrrolidone, 2-vinyl pyrrolidone, etc. Other specific nitrogen heterocycles useful as monomeric starting reagents include N-vinyl-5-methyl-2-oxazolidine, N-vinyl-2-oxazolidone, N-vinyl pyrrolidone, N-vinyl imidazole, N-vinyl-2-methyl imidazole, 2-vinyl imidazole N-vinyl-3-morpholinone, N-vinyl caprolactam, etc. Preferred among these nitrogen heterocycles are the vinyl pyrrolidones.

There generally will be at least about 30 mole percent, and less than about 70%, of the non-nucleophilic monomer unit present in the resin polymer backbone. Typically, the polymer contains from about 45 mole percent to about 55 mole percent of this component.

The crosslinking component of the polymers of the present invention, i.e., the monomer units having A attached thereto in Formula I, can be derived from the monomer:

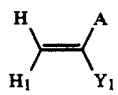

wherein $Y_1$ and A are as defined above. If A is:

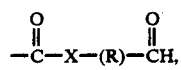

R can be a branched or straight chain aliphatic group. The aliphatic group preferably comprises a methylene or a $C_2$—$C_{18}$ chain, more preferably a methylene or a $C_2$–$C_7$ chain, even more preferably a methylene or a $C_2$ chain. R can be substituted or unsubstituted. Preferably, if R is substituted, the substituent(s) will include an electron withdrawing functionality at the alpha-methylene position relative to the aldehyde group. Suitable electron withdrawing functionalities include, but are not necessarily limited to: halogens, such as chlorine, fluorine, and bromine; amides, such as —NHCOR' wherein each R' can independently be lower chain ($C_1$–$C_{12}$) aliphatic groups, hydroxy groups; alkoxy groups, preferably with short chain ($C_1$–$C_8$) alkyl chains; cyano groups, e.g., —C≡N; and nitro groups, e.g., —$NO_2$. The aldehyde functionality can optionally be chemically protected during polymerization by techniques well-known in the art.

Suitable specific examples of monomers for use include acrolein, methacrolein, 3,3-dimethoxypropyl acrylamide, 3,3-diethoxypropyl acrylamide, 3,3-dimethoxypropyl methacrylamide, 2,2-dimethoxy-1-methylethyl acrylate, 5-(acryloylamino)pentanal dimethylacetal, 8-(acryloylamino)octanal dimethylacetal, 3-(N-acryloyl—N-methylamino)propanal dimethylacetal, 3,3-diethoxypropyl acrylate, 3,3-dimethoxypropyl methacrylate, and 2-(acryloylamino)ethanal dimethylacetal. Acrolein is most preferred. Suitable monomers are also disclosed in U.S. Pat. No. 3,410,828, Kekish issued Nov. 12, 1986 and U.S. Pat. No. 3,317,370, Kekish, issued May 2, 1967, both of which patents are incorporated herein by reference.

The polymers of the present invention can be made by a wide variety of techniques, including bulk, solution, emulsion, or suspension polymerization. Polymerization methods and techniques for polymerization are described generally in *Encyclopedia of Polymer Science and Technology*, Interscience Publishers (New York), Vol. 7, pp. 361–431 (1967), and *Kirk-Othmer Encyclopedia of Chemical Technology*, 3rd edition, Vol 18, pp. 740–744, John Wiley & Sons (New York), 1982, both incorporated by reference herein. See also Sorenson, W. P. and Campbell, T. W., *Preparative Methods of Polymer Chemistry*. 2nd edition, Interscience Publishers (New York), 1968, pp. 248–251, incorporated by reference herein, for general reaction techniques suitable for the present invention. Preferably, the polymers are made by free radical copolymerization, or, more preferably, free radical terpolymerization, using water soluble initiators. Suitable free radical initiators include, but are not limited to, thermal initiators, redox couples, and photochemical initiators. Redox and photochemical initiators are preferred for polymerization processes initiated at temperatures below about 30° C. Such initiators are described generally in *Kirk-Othmer Encyclopedia of Chemical Technology*, 3rd edition, John Wiley & Sons (New York), Vol. 13, pp. 355–373 (1981), incorporated by reference herein. Typical water soluble initiators that can provide radicals at 30° C. or below include redox couples, such as potassium persulfate/silver nitrate, and ascorbic acid/hydrogen peroxide. In one preferred method, water soluble starting monomers are terpolymerized in an aqueous solution polymerization process at room temperature utilizing a redox couple of potassium persulfate and silver nitrate. A more preferred process utilizes thermal initiators in polymerization processes conducted above 40° C. Water soluble initiators that can provide radicals at 40° C. or higher can be used. These include, but are not limited to, hydrogen peroxide, ammonium persulfate, and 2,2'- azobis(2-amidinopropane) dihydrochloride. In one especially preferred method, water soluble starting monomers are terpolymerized in an aqueous alcohol solvent at 60° C. using 2,2'-azobis(2-amidinopropane) dihydrochloride as the initiator. The solvent should typically contain at least about 6% by weight, of alcohol in order to prevent the polymerization reaction medium from gelling. Suitable alcohols for use in such reaction include low molecular weight alcohols such as, but not limited to, methanol, ethanol, isopropanol, and butanol.

Another technique is a solution polymerization as described in U.S. Pat. No. 3,317,370, Kekish, issued May 2, 1967 and U.S. Pat. No. 3,410,828, Kekish, issued Nov. 12, 1968, both incorporated herein by reference. According to such process, the acrolein, or other aldehydic monomer, is copolymerized with a nonnucleophilic, water soluble, nitrogen-heterocyclic polymerizable monomer and a redox initiator system. The copolymer is then made cationic by reacting the copolymer with a water soluble amine or amine quaternary. Amines, including amine quaternaries, that are useful include, but are not limited to, primary, secondary, and tertiary amines such as ethylene diamine, diethylene triamine, triethylene tetramine, tetraethylene pentamine, or partial or fully quaternized derivatives of any of the foregoing, hydrazides and quaternaries thereof such as betaine hydrazide chloride, N-N-dimethylglycine hydrazide, unsymmetrical dimethyl hydrazides, polymers, such as those formed by reaction of urea and polyalkylene polyamines, guanidines, biguanides, guanylureas, mono and polyhydroxy polyamines and quaternaries thereof, etc. When using this emulsion copolymerization technique, it will be necessary to control molecular weight to within the ranges provided herein. Suitable methods for this are discussed below.

Generally, as the molecular weight of the polymer is decreased, initial wet strength will become smaller and wet strength decay will become faster. The temporary wet strength resins of the present invention should have a molecular weight of at least about 20,000, preferably at least about 30,000. The upper limit for molecular weight will be limited by a combination of the ability of the resin to impart the desired level of strength decay, discussed further below, and practical considerations such as sufficiently low viscosity for application to pulp slurries or pulp sheets and technical and economic concerns related to formation of such high molecular weight resins. Generally, the molecular weight should be less than about 200,000, preferably less than about 115,000, and more preferably less than about 95,000.

Molecular weight can be controlled by such methods that are known to those skilled in the art, such as varying reaction temperature (increased temperature typically results in reduced molecular weight), varying free radical initiator concentration, and utilization of chain transfer agents. Suitable chain transfer agents include, but are not limited to, $\beta$-mercaptoethanol, thioglycolic acid, glycerol, acetone, and isopropanol. Other suitable chain transfer agents include, but are not limited to, those described in *Polymer Handbook*, 2nd edition, J. Brandrup and E. H. Immergut, editors, Wiley-Intersciences (New York), (1975), pp. II-57 through II-104, incorporated by reference herein.

The temporary wet strength resins of the present invention are useful for a wide variety of paper and paper products. As used herein, the terms "paper" and "paper products" include sheet-like masses and molded products containing fibrous cellulosic materials which may be derived from natural sources, such as wood pulp fibers, as well as other fibrous material characterized by having hydroxyl groups attached to the polymer backbone. These include glass fibers and synthetic fibers modified with hydroxyl groups. Cellulosic fibers are preferred. In addition, the present invention encompasses papers made from combinations of cellulosic fibers, or other fibers having hydroxyl-substituted polymer chains, and other fibrous or nonfibrous materials known to the art. The paper products of the present invention preferably contain at least about 70%, more preferably at least about 85%, by weight (dry sheet product basis), cellulosic fibers. Suitable nonfibrous additions are described in Young, "Fiber Preparation and Approach Flow" *Pulp and Paper Chemistry and Chemical Technology*, Vol. 2, pp. 881-882, which is incorporated herein by reference.

The resins of the present invention are particularly useful for nonwoven tissue paper products containing cellulosic fibers such as toilet paper, facial tissue, and paper towels. These products will typically have basis weights of between about $8g/m^2$ and about $65g/m^2$, and densities of between about $0.05g/cm^3$ and about $0.60g/cm^3$. They can be made according to any of the techniques known to the art. In forming paper and paper products, the temporary wet strength resins of the present invention are preferably added as dilute aqueous solutions at any point in the papermaking process where wet strength resins are customarily added. The temporary wet strength resins typically are readily absorbed by the cellulose fibers in an aqueous environment at pH values within the range of about 3.5 to about 8.0. The polymer can develop wet strength in paper products within this pH range. For temporary wet strength, i.e., initial wet strength accompanied by desirable wet strength decay rates, the paper is preferably made at a pH within the range of about 3.5 to about 6.0. The wet strength can develop in paper and paper products dried at room temperature or cured at temperatures at which paper is conventionally dried (i.e., typically 85° C.-125° C.).

A substantial amount of initial wet strength is generally imparted to the paper product when from about 0.005% to about 5% of the temporary wet strength resin by weight of the fiber is added. Typically, best results, i.e., about 35% of wet tensile decay at 15 minutes and about 65% at 90 minutes after saturation, are achieved when about 0.25% to about 2.0% of the resin by weight of the fiber is added, and when from 30 mole percent to about 70 mole percent of the non-nucleophilic unit is present in the resin polymer. When lower levels of this unit are added, there is an insufficient amount of wet tensile decay over time. When greater than 70% of the non-nucleophilic unit is present, the paper products typically will not have good initial wet strength. Preferably, for toilet tissue applications particularly, at least about 70% of the initial wet strength decays at 90 minutes after saturation, more preferably at least about 80%.

The temporary wet strength resins of the present invention can be used in any type of tissue paper construction. These include: pattern densified tissue paper such as, but not limited to, that disclosed in U.S. Pat. No. 3,301,746, Sanford and Sisson, issued Jan. 31, 1987, U.S. Pat. No. 3,974,025, Ayres, issued Aug. 10, 1976, U.S. Pat. No. 4,191,609, Trokhan, issued Mar. 4, 1980, U.S. Pat. No. 3,821,068, Shaw, issued June 28, 1974, U.S. Pat. No. 3,573,164, Friedberg et al., issued Mar. 30, 1971, and U.S. Pat. No. 3,994,771, Morgan et al., issued Nov. 30, 1976, all incorporated by reference herein; uncompacted, nonpattern-densified tissue paper such as, but not limited to, that disclosed in U.S. Pat. No. 3,812,000, Salvucci et al., issued May 21, 1974 and U.S. Pat. No. 4,208,459, Becker et al., issued June 17, 1980, both incorporated by reference herein; and conventional tissue paper well known in the art, typically made by pressing a wet web at elevated temperatures to dewater and dry said web.

With respect to tissue paper products, and with particular reference to products such as toilet paper, wherein high levels of softness are desired in addition to good initial wet strength with wet strength decay after the period of usage to low strength levels, it is highly preferred for the paper to have an initial wet strength/dry strength ratio ($WT_i/DT$) of at least about 10%, preferably at least about 12%. Lower ratios are less desirable since the amount of resin that will be added to develop sufficient wet strength will impart undesirably high amounts of dry strength, which reduces toilet softness of the dry paper product.

Additionally, it is desirable for tissue paper products to exhibit a wet strength decay rate after 90 minutes of soaking in neutral pH water of at least about 65%, preferably at least about 70%, even more preferably at least about 80%, as defined according to the following equation:

$$\% \text{ Decay} = \frac{WT_i - WT_R}{WT_i - WT_0} \times 100 \quad (1)$$

wherein $WT_i$ = Initial wet tensile strength of paper with temporary wet strength resin;

$WT_R$ = Wet tensile strength of paper with resin after 90 minutes soaking in neutral pH water; and $WT_0$ = Wet tensile strength of paper without temporary wet strength resin after soaking 90 minutes in neutral pH water.

The tensile strength for the above equation is determined according to the procedure described in the Experimental section below.

EXPERIMENTAL

The following procedures are useful for preparing and testing paper product containing the resins of the present invention.

HANDSHEETS

Handsheets can be formed from 100% unrefined Northern Softwood Kraft (NSK), or other fibers as defined herein. After dispersing the NSK, or other fibers, in distilled water, the temporary wet strength resin is added to the disintegrated pulp and the slurry is agitated for a fixed period of time ranging from 1 to 60 minutes. Handsheets are made essentially according to TAPPI standard T205 with the following modifications:

(1) tap water, adjusted to a desired pH, generally between 3.5 and 6.0, with HCl and/or NaOH is used;

(2) the sheet is formed on a polyester wire and dewatered by suction instead of pressing;

(3) the embryonic web is transferred by vacuum to a polyester papermaking fabric;

(4) the sheet is then dried by steam on a rotary drum drier.

The handsheets are aged a minimum of 24 hours in a conditioned room where the temperature is 73° F.+4° F. (about 22.8° C.+2.2° C. and the relative humidity is 50%+10%. The handsheets should be cut into 1 inch by 5 inch (about 2.5 cm by 12.7 cm) strips using an alfa cutting device for dry and wet tensile testing according to the procedures below.

STRENGTH TEST

1. Dry Tensile Strength

This test is performed on one inch by five inch (about 2.5 cm × 12.7 cm) strips of paper (including handsheets as described above as well as other paper sheets) in a conditioned room where the temperature is 73° F.+4° F. and the relative humidity is 50+10%. An electronic tensile tester (Model 1122, Instron Corp., Canton, Mass.) operated at a crosshead speed of 0.5 inches per minute (about 1.27 cm per min.) and a gauge length of 4.0 inches (about 10.2 cm) is used.

2. Wet Tensile

An electronic tensile tester (Instron 1122) is operated at a crosshead speed of 0.5 inches per minutes and a gauge length of 1.0 inch, using the same size strips as for dry tensile strength testing. The strip is soaked in an aqueous solution containing approximately 23 parts per million (ppm) calcium ion (provided as calcium chloride), 7 ppm magnesium ion (provided as magnesium chloride), and 67 ppm sodium bicarbonate (provided as sodium bicarbonate) in distilled water for the desired soak time, and then measured for tensile strength. As defined herein, initial wet tensile strength is measured when the paper has been saturated for about 5 seconds.

It has been found that the resins in the present invention can provide paper products, such as tissue paper products, which have high $WT_i/DT$ ratios (10%, preferably 12% and higher) while also providing decay rates in excess of 80%. It is not, however, intended to limit the scope of the invention to such tissue paper products.

The following nonlimiting examples are provided to illustrate the present invention. The scope of the invention is to be determined by the claims which follow.

EXAMPLE I

This example shows a redox initiation reaction process for preparing a temporary wet strength resin of the formula:

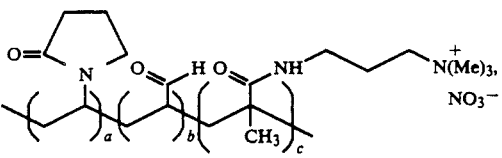

A reaction solution containing N-vinylpyrrolidone (2.78 g, 25.0 mmoles), acrolein (1.41 g, 25.2 mmoles), [3-(methacryloylamino)propyl] trimethylammonium nitrate (0.52 g, 2.11 mmoles), silver nitrate (0.089 g, 0.52 mmoles), and water (35.3 ml) is prepared and placed in a 100 ml round bottom flask equipped with an addition funnel, thermometer, and gas inlet. The reaction solution is swept with argon. Next, a solution of potassium persulfate (0.14 g, 0.52 mmoles) in 5 ml water is added to the reaction solution over a period of one minute with continual stirring, at room temperature. The reaction solution is maintained at between 27° C. and 30° C. by external cooling for a period during which an exothermic polymerization reaction occurs. After the exotherm is subsided, the reaction was stirred for an additional two hours at room temperature, and then transferred to dialysis bags (molecular weight cut-off 3,500). After dialysis against H₂O, the contents of the bags are freeze dried. A temporary wet strength resin product in the form of a white solid should be recovered.

The molecular weight will typically be between about 90,000 and about 95,000. The composition will typically be as follows: a, between about 45% and about 50%; b, between about 45% and about 50%; and c, between about 2% and about 6%.

The value for c can be determined by chloride titration, as described in *Fundamentals of Analytical Chemistry*, B. A. Skoog and D. M. West, Holt, Rinehart, and Winston (1963), p. 253, incorporated by reference herein. The value for a can be determined by reacting all of the aldehyde units of the polymer with Girard's Reagent T and then analyzing for chloride. The value for b can then be calculated as the difference between 100% and the sum of a and b.

Resins of substantially the same composition but different molecular weights can be prepared by, for example, changing the redox initiator couple, or the level thereof, and/or by adding a chain transfer agent.

EXAMPLE II

This example discloses a process for making a resin having substantively the same composition as that of Example I, but a lower molecular weight. The use of an isopropanol chain transfer agent is exemplified.

A reaction solution containing N-vinylpyrrolidone (2.78 g, 25.0 mmoles), acrolein (1.40 g, 25.0 mmoles), 3-(methyacrylamino)propyl]trimethylammonium nitrate (0.52 g, 2.11 mmoles), silver nitrate (0.089 g, 0.52 mmoles), water (10.3 ml), and isopropanol (25.0 ml) is prepared and placed in a 100 ml round bottom flask equipped with an addition funnel, a thermometer, and a gas inlet. The reaction solution is swept with argon. Next, a solution of potassium persulfate (0.14 g, 0.52 mmoles) in 5 ml water is added to the reaction solution over a period of one minute with continual stirring, at room temperature. The reaction solution is then stirred for two hours, without exotherming above 30° C. The reaction solution is transferred to dialysis bags (molecular weight cut-off of 3,500). After dialysis against water for about 16 hours, the contents of the bags are freeze-dried. A temporary wet strength product in the form of a white solid should be recovered.

The values for a, b, and c will typically be in the same ranges as the product of Example I. The molecular weight will typically be between about 30,000 and about 35,000.

EXAMPLE III

This example shows a method useful for preparing temporary wet strength resins within the scope of the invention, having the general formula:

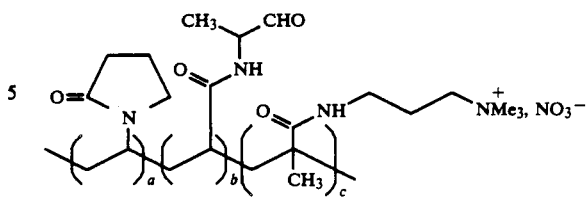

A reaction solution containing N-vinylpyrrolidone (2.78 g, 25.0 mmoles), 2-[methacryloylamino]propanol dimethylacetal (4.71 g, 25.2 mmoles), [3-(methyacrylamino)propyl]trimethylammonium nitrate (0.52 g, 2.11 mmoles), silver nitrate (0.089 g, 0.52 mmoles), water (10.3 ml), and isopropanol (25.0 ml) is prepared and placed in a 100 ml round bottom flask equipped with an addition funnel, a thermometer, and a gas inlet. The reaction solution is swept with argon. Next, a solution of potassium persulfate (0.14 g, 0.52 mmoles) in 5 ml water is added to the reaction solution over a period of one minute with continual stirring, at room temperature. The reaction solution is stirred for an additional two hours at room temperature, and then transferred to dialysis bags (molecular weight cut-off 3,500). After dialysis against H₂O for about 16 hours, the polymer product can be isolated by removing residual solvent under pressure. The acetal can be deprotected to form an aldehyde by dissolving the polymer in 0.020 N aqueous HCl (1.0 g of polymer per 40.0 ml of solution), and heating under an inert atmosphere at 40° C. for two to four hours.

EXAMPLE IV

This example shows a thermal initiation reaction process for preparing a temporary wet strength resin of the formula:

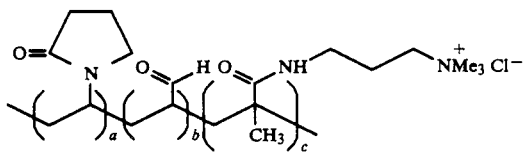

193.6g (0.88 moles) of 3-(methacryloylamino)propyl trimethylammonium chloride is added to a 22 liter reaction flask equipped with an overhead stirrer, condenser, and thermo watch, and containing 8240.0 ml water. After sweeping this solution with nitrogen for about three hours at room temperature, N-vinylpyrolidinone (611.6g, 5.50 moles), acrolein (308.0 g, 5.49 moles), isopropanol (1320.0 g), and 2,2'-azobis(2-amidinopropane) dihydrochloride (29.8 g, 0.11 moles) are added. The reaction is then heated to 60° C. under positive nitrogen pressure. The temperature is maintained at 60° for sixteen hours. After removing the heat source and allowing the reaction to cool, a portion is transferred to a dialysis bag (molecular weight cut-off 3,500). After dialysis against H₂O, the contents of the bag are freeze-dried. A temporary wet strength resin product in the form of a white solid is obtained.

The molecular weight will typically be between about 120,000 to about 130,000. The composition will typically be as follows: a, between about 45% and about 50%; b, between about 45% and about and c, between about 3% and about 6%.

EXAMPLE V

Paper is made according to the teachings of Sanford and Sisson, U.S. Pat. No. 3,301,746, issued Jan. 31, 1967, and U.S. Pat. No. 3,994,771, Morgan and Rich, issued Nov. 30, 1976. The papermachine uses a single headbox with internal partitions ("leaves") which create a discretely layered three-layer paper sheet. The headbox is of the fixed roof former type. The center layer of the sheet is comprised of Northern Softwood Kraft pulp (Grande Prairie, Procter & Gamble Cellulose). This center layer comprises thirty percent (30%) of the total weight of the sheet, and 2.2 lbs. of the temporary wet strength resin of this invention per ton of the pulp (dry fiber basis) is added into this layer. The outside two layers are identical, and each is about 35% of the total sheet weight, dry fiber basis. These layers are comprised of northern Aspen bleached sulfite pulp. The headbox dilution water (the "wire pit" water) is natural water which is acidified with HCl to an approximate pH of from about 5.5 to 5.9. The discretely layered sheets are formed on a polyester 84 M. This wire is an "84M"; that is, the weave was (84×76 filaments per inch) wire woven in a five-shed pattern to form an embryonic web. The embryonic paper web is transferred to a 36×32 five-shed fabric. These patterns and their use are described in Trokhan, U.S. Pat. No. 4,191,609, and Trokhan, U.S. Pat. No. 4,239,065, both of which are incorporated by reference herein.

The embryonic paper sheet is first dried with hot air in a flow-through dryer to a moisture level of about 35% by weight of the sheet. Such a hot air dryer is well known to those skilled in the art. The final drying is accomplished on the surface of a Yankee dryer (to which the web has been adhered with polyvinyl alcohol). The paper is dried to approximately 3% moisture, and then creped from the Yankee with a doctor blade zone and reeled to provide an ultimate residual crepe of about 20%.

What is claimed is:

1. A paper product comprising a sheet of fibrous materials and from about 0.005% to about 5.0% of a water soluble, temporary wet strength resin, said resin comprising a polymer characterized by the substantially complete absence of nucleophilic functionalities and having the formula:

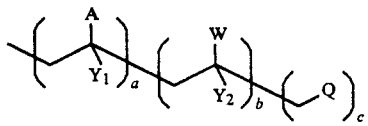

wherein: A is

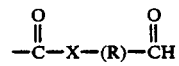

and X is —O—, —NH, or —NCH$_3$—, and R is a substituted or unsubstituted aliphatic groups; Y$_1$ and Y$_2$ are independently —H, —CH$_3$ or a halogen; W is a nonnucleophilic, water-soluble nitrogen heterocyclic moiety; O is a cationic monomeric unit; the mole percent of a is from about 30% to about 70%, the mole percent of b is from about 30% to about 70%, and the mole percent of c is from about 1% to about 40%; and said polymer has an average molecular weight of between about 30,000 and about 200,000.

2. A paper product as in claim 1, wherein a is from about 45% to about 55%, b is from about 45% to about 55%, and c is from about 2% to about 20%, said sheet having an initial wet tensile strength/dry tensile strength ratio of at least about 10% and a wet tensile decay rate after 90 minutes soaking in neutral pH water of at least about 70%.

3. A paper product comprising a sheet of fibrous materials and from about 0.005% to about 5.0% of a water soluble, temporary wet strength resin, said resin comprising a polymer characterized by the substantially complete absence of nucleophilic functionalities and having the formula:

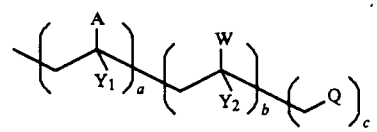

wherein: A is

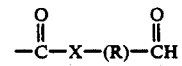

and X is —O—, —NH, or —NCH$_3$—, and R is a substituted or unsubstituted aliphatic group; Y$_1$ and Y$_2$ are independently —H, —CH$_3$ or a halogen; W is a nonnucleophilic, water-soluble nitrogen heterocyclic moiety; O is a cationic monomeric unit; the mole percent of a is from about 30% to about 70%, the mole percent of b is from about 30% to about 70%, and the mole percent of c is from about 1% to about 40%; and said polymer has an average molecular weight of between about 30,000 and about 200,000.

4. A paper product as in claim 3, wherein a is from about 45% to about 55%, b is from about 45% to about 55%, and c is from about 2% to about 20%.

5. A paper product as in claim 2, wherein W is a vinyl pyrrolidone and X is —NH or —NCH$_3$, said sheet having an initial wet tensile strength/dry tensile strength ratio of at least about 12% and a wet tensile decay rate after 90 minutes soaking in neutral pH water of at least about 70%.

6. A paper product as in claim 5, wherein said sheet has an initial wet strength/dry tensile strength ratio of at least about 12% and a wet tensile decay rate after 90 minutes soaking in neutral pH water of at least about 80%.

7. The paper product of claim 1, wherein said resin comprises less than 3 mole % of monomer units having nucleophilic functionalities.

8. The paper product of claim 5, wherein said resin comprises less than about 1 mole % of monomer units having nucleophilic functionalities.

9. The paper product of claim 6, wherein said resin comprises less than about 1 mole % of monomer units having nucleophilic functionalities.

10. The paper product of claim 8, wherein said resin has 0 mole % of monomer units having nucleophilic functionalities.

* * * * *